United States Patent
Shay (10) Patent No.: US 10,780,221 B2
(45) Date of Patent: Sep. 22, 2020

(54) PULSE INFUSION DEVICE SYSTEM AND METHOD

(71) Applicant: Medical Flow Systems Ltd., Shlomi (IL)

(72) Inventor: Ofer Shay, Kfar Vradim (IL)

(73) Assignee: Medical Flow Systems Ltd., Shlomi (IL)

( * ) Notice: Subject to any disclaimer, the term of this patent is extended or adjusted under 35 U.S.C. 154(b) by 92 days.

(21) Appl. No.: 16/122,938

(22) Filed: Sep. 6, 2018

(65) Prior Publication Data

US 2019/0001056 A1 Jan. 3, 2019

Related U.S. Application Data

(60) Division of application No. 14/685,711, filed on Apr. 14, 2015, now Pat. No. 10,086,137, which is a continuation-in-part of application No. 13/811,348, filed as application No. PCT/IL2011/000591 on Jul. 21, 2011, now abandoned.

(Continued)

(51) Int. Cl.
*A61M 5/168* (2006.01)
*A61M 5/142* (2006.01)

(52) U.S. Cl.
CPC .... *A61M 5/16881* (2013.01); *A61M 5/14212* (2013.01); *A61M 5/14216* (2013.01)

(58) Field of Classification Search
CPC .......... A61M 5/14276; A61M 5/14248; A61M 5/142; A61M 5/14216; A61M 5/172;

(Continued)

(56) References Cited

U.S. PATENT DOCUMENTS

| 3,731,679 A | 5/1973 | Wilhelmson et al. |
| 4,034,754 A | 7/1977 | Virag |

(Continued)

FOREIGN PATENT DOCUMENTS

| EP | 0160303 | 11/1985 |
| WO | WO 2009/149367 | 12/2009 |
| WO | WO 2012/011115 | 1/2012 |

OTHER PUBLICATIONS

European Search Report of European Application No. 16779710 dated Sep. 7, 2018.

(Continued)

*Primary Examiner* — Manuel A Mendez
(74) *Attorney, Agent, or Firm* — Pearl Cohen Zedek Latzer Baratz LLP (57) ABSTRACT

Aspects of the invention are related to a method and a system for administrating an infusion liquid pulse. The system includes a tubing system having an inlet connected to an external reservoir adapted to contain infusion fluids and an outlet connected to a catheter. The tubing system includes a check valve proximate to the inlet and an anti-siphon valve proximate to the outlet. The system further includes an automatic pulse flow generation device. The automatic pulse flow generation device includes an internal reservoir and a bidirectional pump configured to pump infusion fluid from the external reservoir to the internal reservoir and further pump an infusion fluid pulse from the internal reservoir to be injected by the catheter, the infusion liquid pulse has a volume of at least 2 ml and a velocity of at least 5 ml/min.

11 Claims, 12 Drawing Sheets

Related U.S. Application Data (60) Provisional application No. 61/382,797, filed on Sep. 14, 2010, provisional application No. 61/366,688, filed on Jul. 22, 2010.

(58) Field of Classification Search
CPC ............ A61M 5/14244; A61M 5/1723; A61M 5/1454; A61M 5/007; A61M 5/1456; A61M 5/16827; A61M 5/1424; A61M 5/1452; A61M 5/14224
See application file for complete search history.

(56) References Cited

U.S. PATENT DOCUMENTS

| | | |
|---|---|---|
| 4,668,220 A | 5/1987 | Hawrylenko |
| 5,009,641 A | 4/1991 | Gorton |
| 5,643,213 A | 7/1997 | McPhee |
| 2003/0229310 A1* | 12/2003 | Flaherty .............. A61M 5/1452 604/151 |
| 2011/0209764 A1 | 9/2011 | Uber et al. |
| 2013/0035659 A1 | 2/2013 | Hungerford et al. |
| 2013/0123703 A1 | 5/2013 | Shay |
| 2013/0345659 A1* | 12/2013 | Shay ................. A61M 5/16804 604/500 |
| 2015/0217049 A1 | 8/2015 | Shay |

OTHER PUBLICATIONS

International Preliminary Examination Report of International Application No. PCT/IL2017/050348 dated Oct. 11, 2018.
Chinese Office Action of Chinese Application No. 2017800330450 dated Jul. 23, 2019.

* cited by examiner

PULSE INFUSION DEVICE SYSTEM AND METHOD

CROSS REFERENCE TO RELATED APPLICATION

This application is a divisional of application Ser. No. 14/685,711, filed Apr. 14, 2015 which is a continuation-in-part of application Ser. No. 13/811,348, filed Jan. 21, 2013, which is a National Phase Application of PCT International Application No. PCT/IL2011/000591, International Filing Date Jul. 21, 2011, which claims the benefit of U.S. Provisional Patent Application No. 61/382,797, filed Sep. 14, 2010 and U.S. Provisional Patent Application No. 61/366,688, filed Jul. 22, 2010, each of which is incorporated herein by reference.

FIELD OF INVENTION

The present invention relates to the administration of liquid medicines. More particularly there is disclosed a pulse infusion pump which is programmable to suit the volume, the velocity and frequency as directed by the doctor in charge of the patient and/or by the patient him/herself in pain control applications.

BACKGROUND OF THE INVENTION

Since the early 90's the use of infusion pumps to administer anesthetics has become common practice for achieving continuous regional and local anesthesia. These pumps are either electro-mechanical pumps or mechanical pumps. Most pumps are designed to be ambulatory, carried by the patient in a pouch or similar holder. Some types of pump are suitable for Patient Control Analgesia (PCA) whereby the patient can add additional medication bolus to the basal flow to address severe pain.

Currently there are two main clinical procedures that are used for continuous long-term postoperative regional/local anesthesia, both are subcutaneous/intramuscular. The first procedure is Surgical Site Infiltration (SSI), wherein the medication is introduced into or nearby the surgical incision by use of a catheter with a long fenestrated segment inserted into the patient tissue. The second procedure is Continuous Peripheral Nerve Block (CPNB), wherein medication is introduced proximate to the nerve that controls the limb that has been operated. When CPNB administration is performed, an efficient pain block is achieved due to medication saturation of an area surrounding the nerve. Therefore, maintaining sufficient nerve bathing is essential to gain continuous pain blockage. For example, such sufficient nerve bathing is achieved when a nerve block is performed by manual injection, typically performed prior to surgery. One of the main objectives of the present innovation is to continuously maintain sufficient nerve bathing through implementing an innovative infusion strategy for CPNB and thereby gain an improved post-operative pain therapy.

Automatic pumps for continuous medication insertion are well known in the art, for example, insulin pumps. Such devices are configured to continuously inject small amounts of medication, for example, in the order of 1 ml/hour (0.017 milliliter/minute), intravenously (IV) into a human venous. The amounts of medication injected intravenously must be closely controlled as not to harm the venous while continuously injecting the medication. Other IV pumps known in the art can inject larger amount of medication even up to 30 ml/min, however such pumps are not designed to endure pressures higher than 0.2 bar. Such pumps do not suit regional/local anesthesia that requires rapid injection of relatively large amount of anesthetic medication at a relative rapid velocity that is administrated through relative thin and long catheter; requires relatively high pressure, for example, volume of more than 2 ml in a velocity of at least 5 ml/min with 20 G catheter 50 to 100 cm long required a pressure of at least 2.5 bar.

SUMMARY OF THE INVENTION

The device of the invention provides infused medication in a continuous pulse flow at a defined volume and frequency and velocity while maintaining a stable and accurate average flow rate. The device is particularly useful for large volume pulses at low frequency.

Embodiments of the invention may be related to a system for administrating an infusion liquid pulse. The system may include a tubing system having an inlet connected to an external reservoir adapted to contain infusion fluids and an outlet connected to a catheter. The tubing system may further include a check valve proximate to the inlet and an anti-siphon check valve proximate to the outlet. The system may further include an automatic pulse flow generation device. The automatic pulse flow generation device includes an internal reservoir and a bidirectional pump configured to pump infusion fluid from the external reservoir to the internal reservoir and further pump an infusion fluid pulse from the internal reservoir to be injected through a catheter, the infusion liquid pulse has a volume of at least 2 ml and a velocity of at least 5 ml/min.

Other embodiments of the invention may be related to a method of administrating an infusion liquid pulse. The method may include automatically pumping an infusion liquid from an external reservoir to an internal reservoir included in a pulse infusion system, the external reservoir may be adapted to contain infusion fluids and automatically generating the infusion liquid pulse by pumping from the internal reservoir a predetermined volume of an infusion liquid and injecting the predetermined volume at a predetermined velocity, the predetermined volume is at least 2 ml and the predetermined velocity is at least 5 ml/min.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Figure 1A:
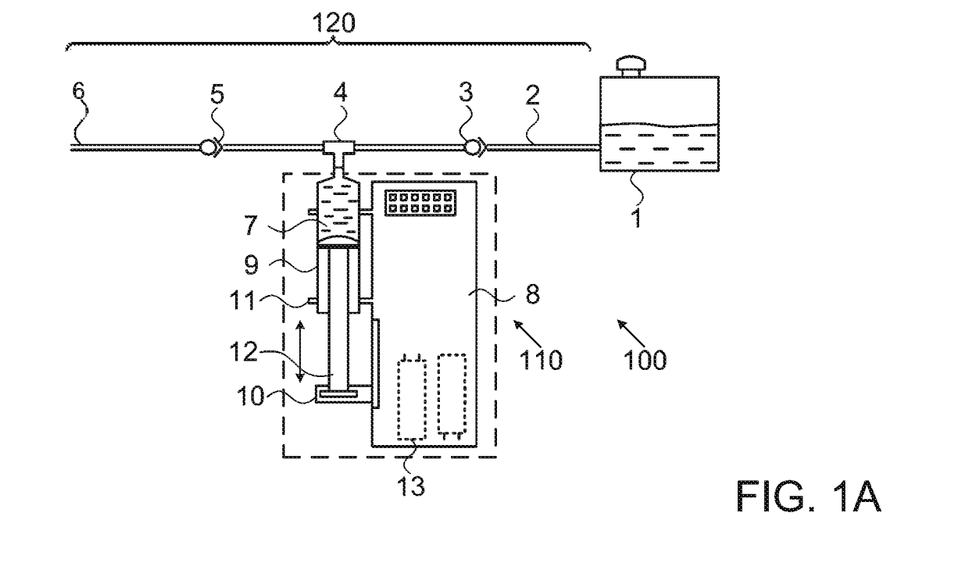
FIGS. 1A and 1B are schematic illustrations of an electro-mechanical pulse infusion system according to one embodiment of the present invention in a pre-pulse position and in a post-pulse position according to some embodiments of the invention.
Figure 1B:
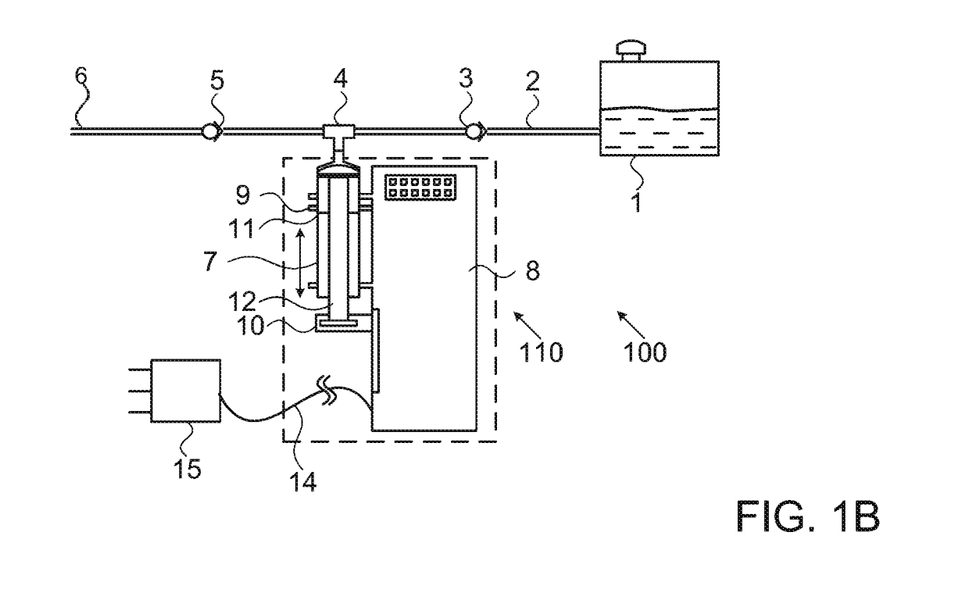

System 100, which is illustrated in FIGS. 1A and 1B, is a stand-alone electro-mechanical infusion system that creates pulsed flow having high volume and high velocity. According to some embodiments of the present invention system 100 may allow a user to set the volume of the pulse, the frequency of the pulses and the pulse velocity.

According to one embodiment of the present invention, system 100 may include a tubing system 120 having an inlet 2 connected to an external reservoir 1 adapted to contain infusion fluids and an outlet 6 connected to a catheter (not illustrated). External reservoir 1 may be a fluid medication reservoir; solid, semi-solid container or a bag. System 100 may be an automatic pulsed flow generation device 110. According to some embodiments of the present invention, tubing system 120 may be a disposable tubing system. Tubing system 120 may further include a check valve 3 proximate to inlet 2 and an anti-siphon check valve 5 proximate to outlet 6.

Automatic pulse flow generation device 110 may include an internal reservoir 7, for example, in a form of a tube of a syringe, and a bidirectional pump 12. Bidirectional pump 12 may include a piston (as illustrated in FIG. 1A) and a pulse actuation apparatus 8. It should be understood by those skilled in the art that the piston illustrated in FIG. 1A is given as an example only, and that other bidirectional pumps are in the scope of the present invention. According to other or additional embodiments automatic pulsed flow generation device 110 may be programmable by a user such as a medical team and/or a patient. According to yet another embodiment of the present invention, automatic pulsed flow generation device 110 may be pre-set. Bidirectional pump 12 may be configured to pump infusion fluid from external reservoir 1 to internal reservoir 7 and further pump an infusion fluid pulse from internal reservoir 7 to be injected by the catheter, the infusion liquid pulse may have a volume of at least 2 ml and a velocity of at least 5 ml/min at pulse cycle frequency of 15 minutes or longer.

An exemplary automatic pulsed flow generation device 110 may comprise an internal pump reservoir 7, such as a syringe, a piston 12 and a pulse actuation apparatus 8. During the bidirectional operation syringe 7 is filled and emptied during each cycle.

Device 110 may further include a controller (not illustrated) configured to control bidirectional pump 12 and optionally also valves 3 and 5. In some embodiments, the controller may control pulse actuation apparatus 8 included in pump 12 to control the velocity of the infusion pulse, for example to generate or provide an infusion pulse having a velocity of 5-30 ml/min (milliliter/minute). In some embodiments, the controller may control pulse actuation apparatus 8 included in pump 12 to control the volume of the infusion pulse, for example, to generate or provide an infusion pulse having a volume of 2-15 ml (milliliter). In some embodiments, the controller may control pulse actuation apparatus 8 included in pump 12 to control a frequency at which the pulses are injected, for example, the pulse may be given to a patient between once in every 90 minutes to once in every 10 minutes. The controller may further control the internal pressure at which the pulse is injected. A relatively high pressure, for example, of at least 1.5 or 2 bar may be required to produce a pulse at a velocity of at least 5 ml/min. The controller may control pump 12 to build a pressure of at least 2 bar in order to inject the pulse at at least 5 ml/min.

The controller may control pump 12 to pump infusion fluid from external reservoir 1 to internal reservoir 7 while opening valve 3. In another embodiment, the controller may control pump 12 to generate an infusion fluid pulse by pumping the infusion fluid from internal reservoir 7 to outlet 6 while opening anti siphon check valve 5.

According to one embodiment of the present invention, internal reservoir 7 is filled using energy provided by the flow from external reservoir 1. It would be appreciated by those skilled in the art that other mechanisms may be used for filling internal reservoir 7 with fluid received from external reservoir 1.

According to one embodiment of the present invention, pulsed flow generation device 110 may be operated electro-mechanically, through an electric motor or solenoid (not shown) which may be controlled by an electronic controller (not shown) in actuation apparatus 8. The electronic controller may be programmable or preprogrammed to allow adapting the pulses frequency, the volume and velocity of each pulse of fluid and other parameters in order to tailor these parameters to the needs of each patient.

In some embodiments, device 110 may include more than one controller. For example, actuation apparatus 8 may comprise a controller for controlling the pulses frequency (not shown). According to another embodiment of the present invention, actuation apparatus 8 may comprise another or an additional controller such as a pulsed flow volume controller. Additionally, actuation apparatus 8 may comprise a flow velocity controller. It would be appreciated by those skilled in the art that other controllers, optionally of other parameters, may be used.

Pulsed flow generation device 110 may pump a defined volume of fluid, for example, 10 ml, received from external reservoir 1 to an internal pump reservoir, such as syringe 7. Pump 12 (e.g., a piston) may then pump out that defined volume or a smaller volume, for example, 5 ml, entirely or partially, into a catheter (not shown) placed in the body of the patient. These pumping operations may be performed continuously at a selected frequency, for example, once every 60 minutes.

According to one embodiment of the invention both internal reservoir 7 and pump 12 may be parts of a disposable syringe set. Device operation parameters can be preset during manufacturing (pre-programmed) or, in a programmable version, the medical team may have the option to select and set the operational parameters of the device during the course of the therapy and to permanently lock them when needed.

In some embodiments, the device may be an ambulatory type powered by batteries 13. However a stationary device can be used where the patient is unlikely to be moved. Energy may then be supplied through a cord 14 connected to the building electric supply via a transformer-rectifier 15.

In some embodiments the system may be operated manually by the patient and/or medical team in addition to the automatically pulses delivery. In some embodiments, the system may be operated manually only by the patient and/or medical team. In some embodiments, when operated manually system 100 may be configured to supply an infusion liquid pulse having a volume of at least 2 ml and a velocity of at least 5 ml/min.

FIG. 1A represents an electromechanical pulsed flow generation device 110. Tubing system 120 compromise inlet tube 2 that may be connected at one end to external reservoir 1 by use of a standard fitting and on the other end to check valve 3. A connector, such as a T shape connector 4, may be positioned between said check valve and an anti-siphon check valve 5. Outlet port 6 may be positioned after said anti-siphon check valve. Outlet port 6 may have standard fitting to be connected to an NB catheter placed in the patient body or any other fluid insertion apparatus known in the art. The remaining branch of T connector 4 opens into variable volume container such as a standard disposable syringe 7. It would be appreciated by those skilled in the art that actuation apparatus 8 of device 110 may be disposable or reusable, while tubing system 120 and external reservoir 1 are usually disposable components.

Internal reservoir 7 may be connected to electromechanical programmable actuation apparatus 8 by mounting the reservoir barrel 11 onto a holder 9 and the piston rod 12 to the pull lever 10.

Check valve 3 may further prevent back-flow of fluids from connector 4 to external reservoir 1. Anti-siphon check valve 5 may further prevent gravity flow from reservoir 1 to exit port 6 and prevents back flow from exit port 6 to connector 4.

Pull lever 10 of actuation apparatus 8 may move linearly only along one axis of pump 12 (in the direction of the double-headed arrow indicated in FIGS. 1A and 1B) so that when pull lever 10 moves in a first direction, the internal volume of internal reservoir 7 increases and when pull lever 10 moves in a second direction the volume of internal reservoir 7 decreases.

Movement in the first direction of the pull lever 10, driven by the actuation apparatus 8, draws the pump (e.g., piston) 12 in the same first direction, creating a vacuum in the cylinder of syringe which serves as internal intermittent reservoir 7. As a result fluid is drawn from reservoir 1 into internal reservoir 7.

Movement of pull lever 10 in said second direction applies pressure on the fluid in internal reservoir 7 that pumps out the medication from said internal reservoir 7 to the patient through anti-siphon check valve 5 and through outlet port 6.

Electronic programmable means of actuation apparatus 8 may enable to determine the volume that to be pumped into syringe 7 every and each movement cycle of pull lever 10 (e.g., 15 ml) in the first direction and the volume that is pumped out of syringe 7 (e.g., 5 ml) every and each movement of pull lever 10 in the second direction. Frequency of pull lever 10 movement may also be pre-set and controlled. Similarly, the speed of movement of pull lever 10 may also be pre-set and controlled.

According to some embodiments of the present invention, actuation apparatus 8 may be equipped with electronic means to store and analyze the infusion data and to sound an alarm when data received and recorded is outside predefined limits. For example, when the total pulsed flow volume is beyond a predefined maximum dosage.

FIG. 1B shows the electromechanical pulse infusion system 100, presenting the system in a situation where the pull lever 10 has moved in the second direction to its extremity, i.e. pumping out the fluids within syringe 7. According to the embodiment illustrated in FIG. 1B, device 110 may be arranged to receive power from a wall socket, using a transformer-rectifier 15 and a cable 14.

Figure 1C:
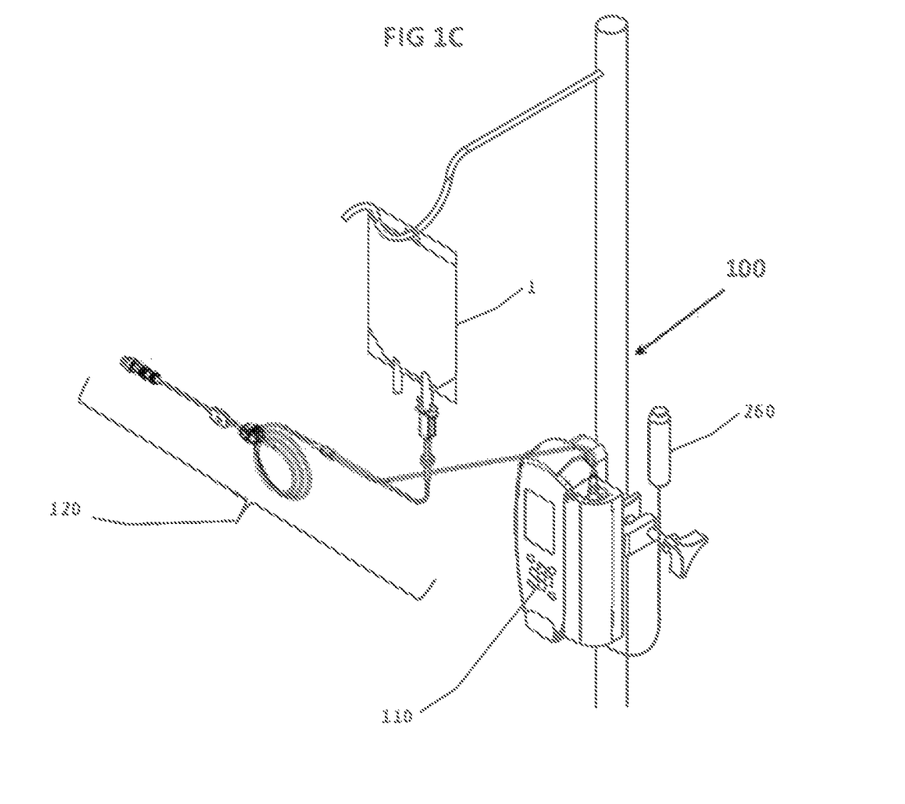
FIGS. 1C and 1D are schematic illustrations of stationary and ambulatory electro-mechanical pulse infusion systems, respectably, according to some embodiments of the invention.

Reference is made to FIG. 1C that is a schematic illustration of a stationary pulse infusion system 100 according to some embodiments of the invention. External reservoir 1 in a form of a plastic bag may be placed on a pole near or above a patient's bad. Tubing system 120 may connect the bag to system 100 and may further be connected to a catheter. System 100 may further include a manual pulse flow controlling device 260, allowing the patient and/or medical team member to manually control pulse flow generation device 110 to give an additional pulse of medication upon the patient's request (regardless of the administration frequency determined and programed in the automatic pulse flow generation device).

In some embodiments, System 100 may be configured to deliver manual pulse flow only.

Figure 1D:
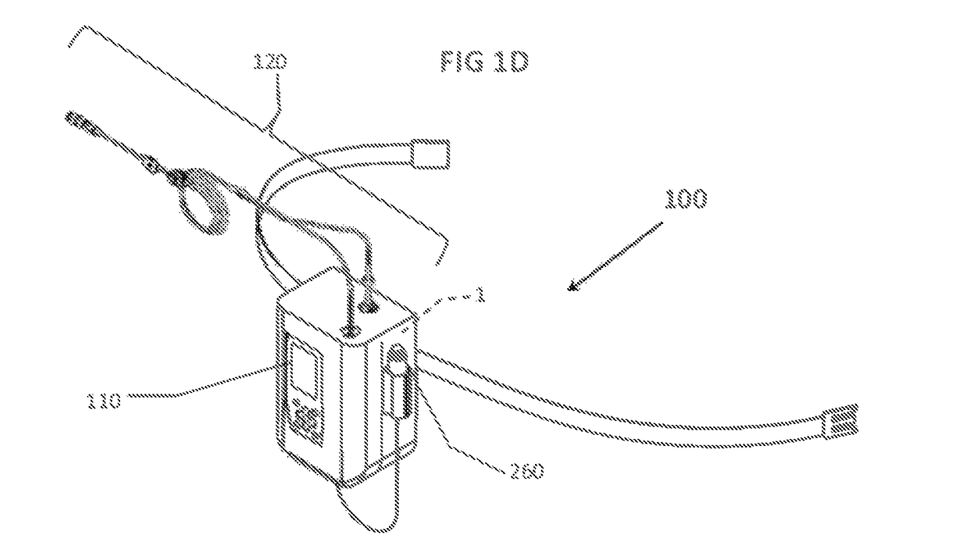

Reference is made to FIG. 1D that is a schematic illustration of an ambulatory pulse infusion system 100 according to some embodiments of the invention. External reservoir 1 may be placed inside or attached to the body of system 100 to be carried out by the patient. An ambulatory system 100 may further include a tubing system 120 and a manual pulse flow controlling device 260 as disclosed above.

Figure 2:
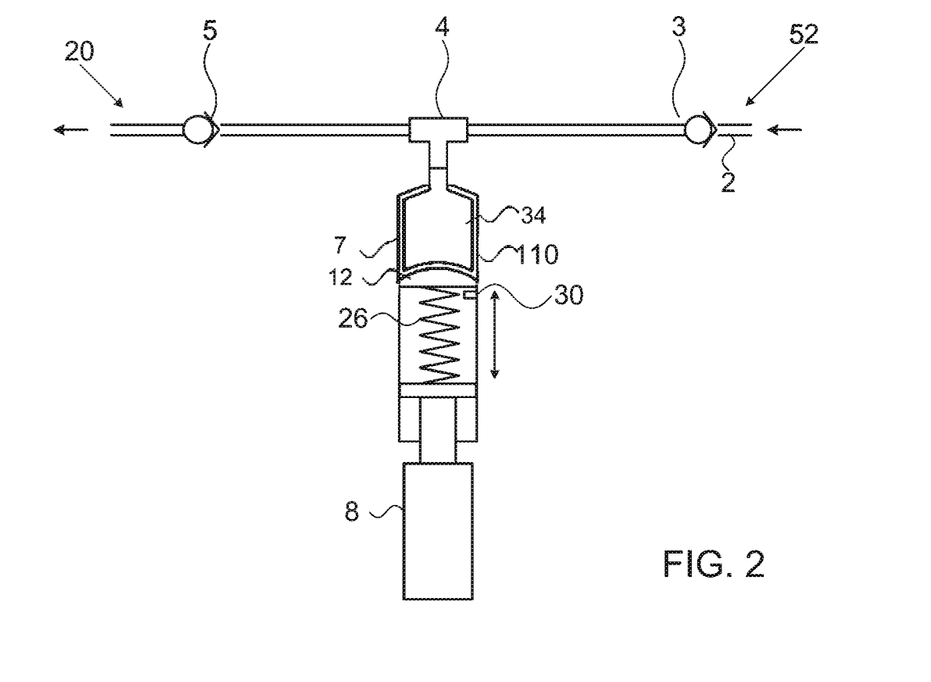
FIGS. 2, 3, 4, 5, 6A, 6B, 7A and 7B are schematic illustrations of additional exemplary mechanical and electro-mechanical pulse infusion devices according to some embodiments of the present invention.

Reference is now made to FIG. 2 which is a schematic drawing of another electromechanical embodiment of the present invention. As may be seen in FIG. 2, tubing 2 is connected to an inlet port 52 through an optional one-way valve 3. A connector such as a T shape connector 4 leads to an anti-siphon check valve 5 and an exit port 20.

Pulse flow generation device 110 is also connected to the 'T' connector 4. Pulsed flow generation device 110 is equipped with a pump (e.g., piston) 12, an optional spring 26, an electric actuation apparatus 8 and a sensor (proximity switch) 30. Syringe 7 is filled and discharges through connector 4.

A fluid, such as fluid medicament, may flow from an infusion pump (not shown) through inlet port 52, and through valve 3. The fluid flowing into tube 2 between valves 3 and 5 may cause pressure build-up and push piston 12 in the first direction to increase the volume of fluid that may be contained in syringe 7. When the volume of fluid within syringe 7 reaches a predefined volume, actuation apparatus 8 causes piston 12 to start moving in a second direction to pump out the fluid contained in syringe 7. When fluid is pumped out from syringe 7 into tube 2, pressure in tube 2 increases until pressure check valve 5 is opened, and a pulse of fluid may flow through the pressure-activated check valve 5 and may exit into a patient's body through outlet port 20.

According to one embodiment of the present invention, as piston 12 reaches the vicinity of proximity switch 30 an electric signal causes actuation apparatus 8 to move in a second direction and applies an additional force on compression spring 26. Spring 26 in turn pushes liquid out of device 110 forcing valve 5 to open and release a pulse of fluid medication. Spring 26 acts as a buffer between the fast actuation apparatus 8 and the slower movement of the piston 12. According to yet another embodiment of the present invention, actuation apparatus 8 retracts to its original position after a preset delay, typically between 1 and 3 seconds. The reduced fluid pressure in syringe 7 allows new fluid therein thus starting a new cycle.

It would be appreciated by those skilled in the art that spring 26 may not be required and other buffer mechanisms may be used. It would be further realized that a buffer may not be required at all.

Means are provided to change the position of sensor or proximity switch 30, thus adjusting the pulsed fluid volume. Other means for adjusting the volume of fluid released in each pulse may be used.

In an alternative embodiment sensor 30 is a component which continuously monitors piston 12 position and transmits signals to a programmable controller (PEC) (not illustrated). The PEC is easily set to a desired fluid volume per pulse, and additionally any desired time delay can be programmed therein.

Figure 3:
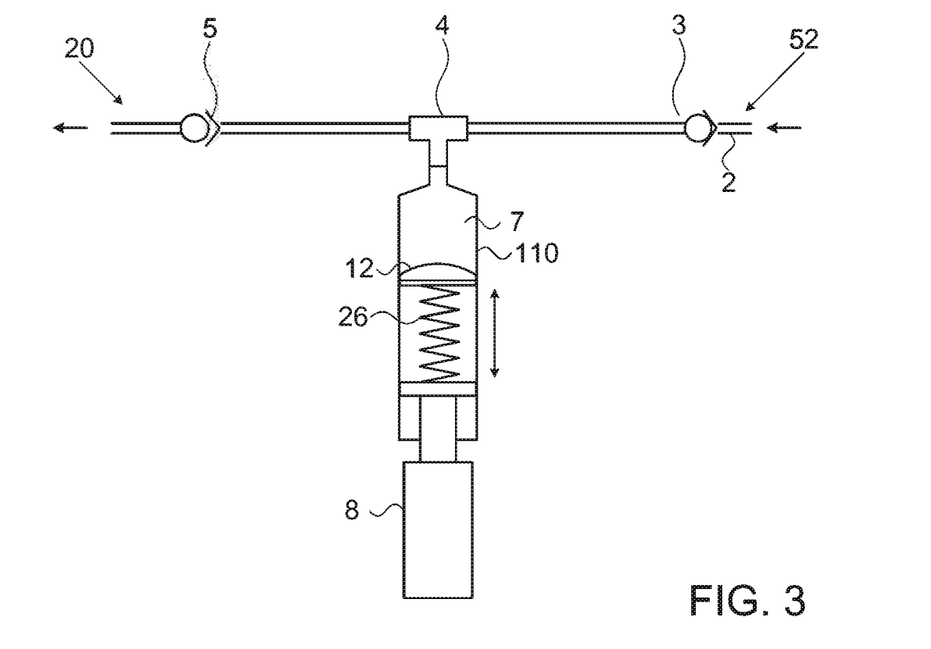

Referring now to FIG. 3 that is an illustration of a pulse flow generation device 110 according to some embodiments of the invention. Device 110 of FIG. 3 is almost identical to that seen in FIG. 2 except that no sensor (proximity switch) is provided. A PEC (not shown) controls the actuation apparatus 8, generating an electric signal according to a time interval set by the medical team. The signal connects power to the actuation apparatus 8 to move in a second direction to pump out fluid from syringe 7 and the pulse is generated exactly as described with reference to FIG. 2. The time interval set in the PEC may be easily changed, and thus different pulsed volumes can be ejected while using the same basic flow rate.

Figure 4:
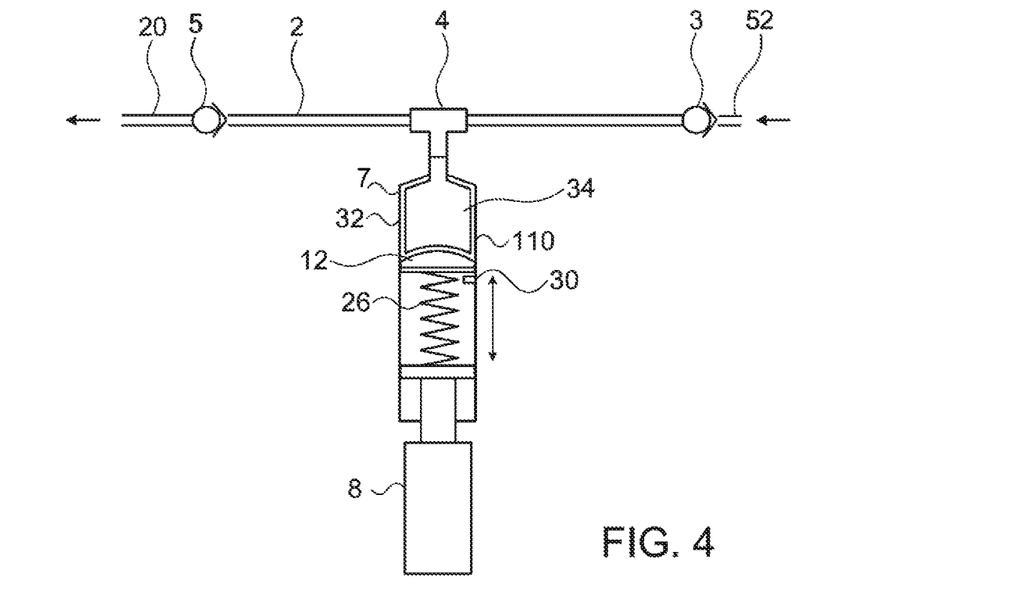

Turning now to FIG. 4, which illustrates an embodiment provided with a syringe 7 having an internal container 34 made of an elastic material, for example of silicone rubber positioned inside a rigid container 32. Internal container 34 has a controlled volume and is beneficial in preventing any leak of a fluid into the pump mechanism. Furthermore, internal container 34 reduces the area of contact between the fluid and parts of the pump. In all other respects the present embodiment is identical to the embodiment described with reference to FIG. 2.

Figure 5:
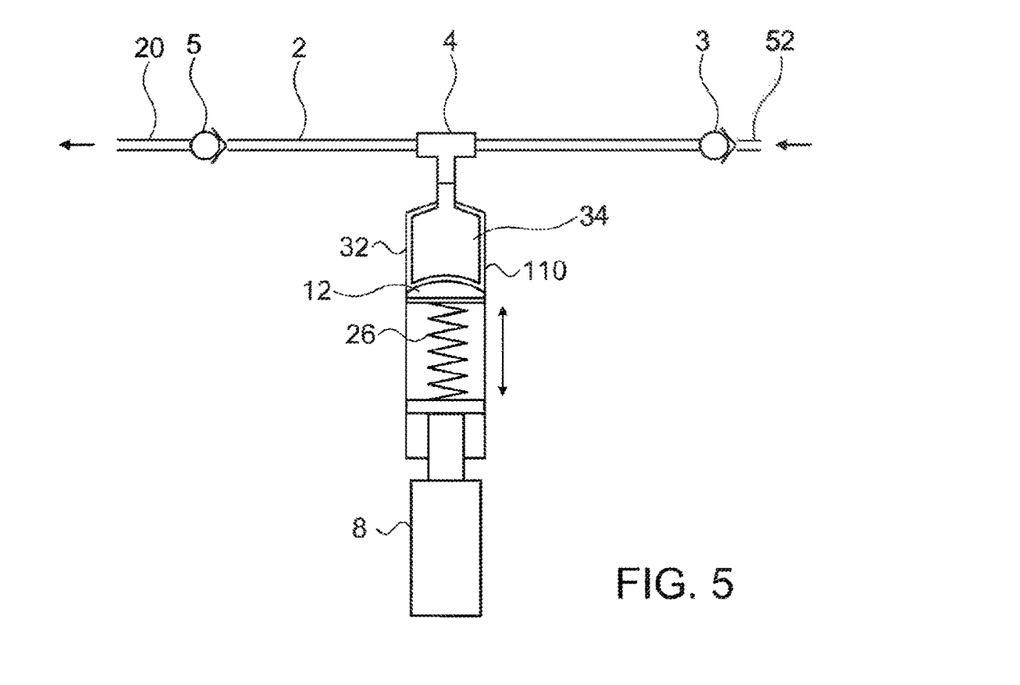

With regard to FIG. 5, which illustrates an embodiment similar to that shown in FIG. 4, except that a PEC (not shown) comprised within actuation apparatus 8 creates an electric signal according to a time interval set by the user. Therefore switch or sensor 30 seen in FIG. 4 may not be required.

Figure 6A:
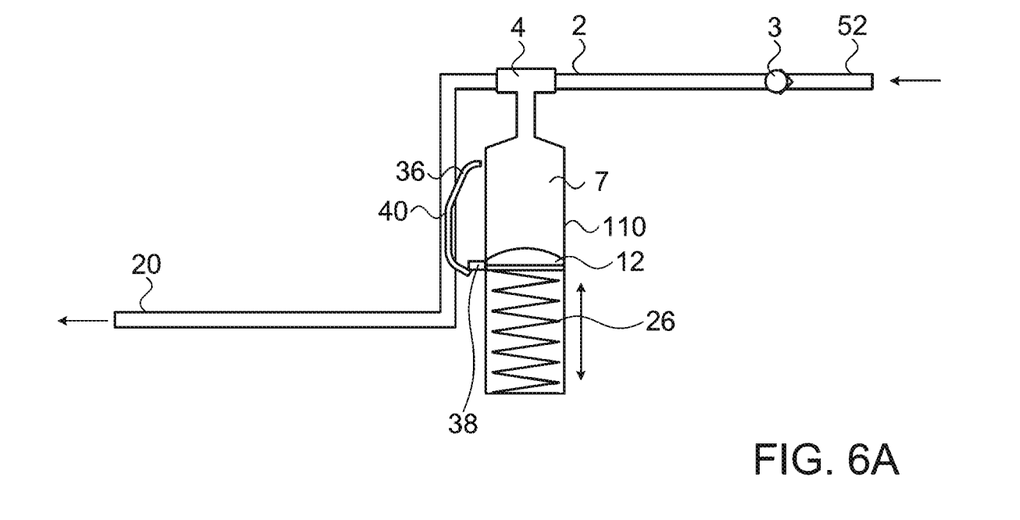
Figure 6B:
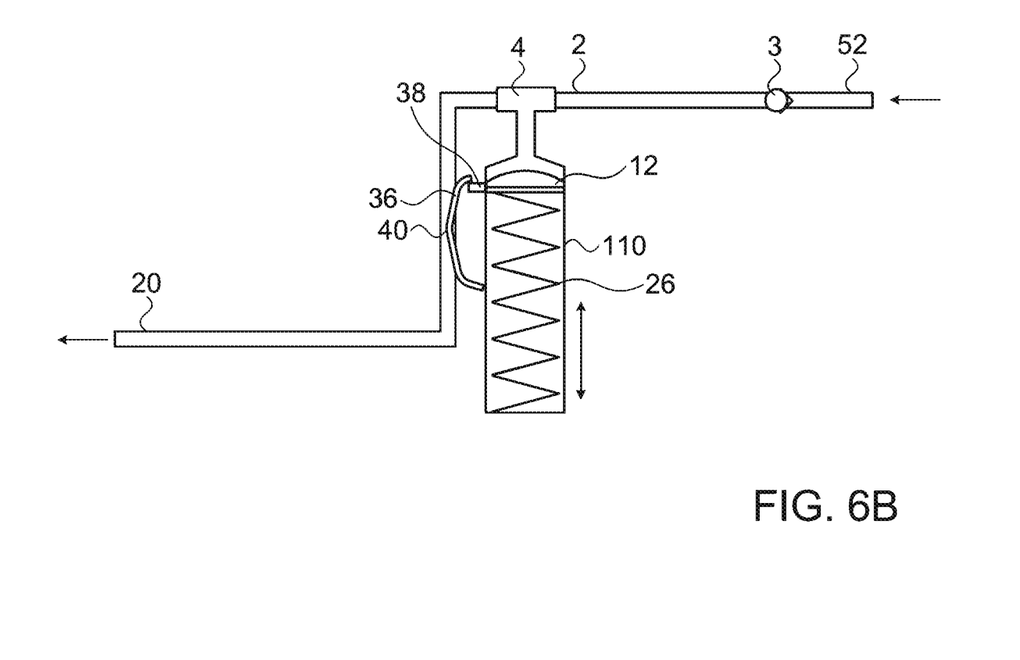

FIGS. 6A and 6B illustrate a mechanical pulse device, so there is no electric actuation apparatus 8 as was seen in previous embodiments.

Tubing 2 is connected to an inlet port 52 through an optional one-way valve 3. A connector such as T shaped connector 4 leads to a pressure-activated check valve 40 and an exit port 20.

Pulsed flow generation device 110 is also connected to the 'T' connector 4. Pulsed flow generation device 110 may be equipped with a piston 12, a spring 26, and a projection 38.

The normally closed valve 40 thus prevents fluid discharge through outlet port 20, wherefore incoming fluid accumulates in syringe 7.

Valve 40 may be actuated by a lever 36 when pushed by projection 38.

A fluid, such as a fluid medicament may flow from an infusion pump (not seen) through inlet port 52. During pressure build up in connector 4 and in the syringe 7 piston 12 moves in a first direction to increase the volume of fluid contained in syringe 7 until projection 38 contacts a part of lever 36, opening valve 40 and forcing a pulse of liquid through port 20.

The reduced fluid pressure in syringe 7 then allows the entry of new fluid into syringe 7 thus starting the next cycle.

Means are provided to change the position of the projection 38 relative to the dimensions of pulse flow generation device 110, thus adjusting the pulse volume. According to another embodiment, two projections, lower and upper may be used instead of projection 38. The lower projection can be adjusted by the medical team member for varying the pulse volume. It would be appreciated that other means for adjusting the pulsed volume may be used.

Figure 7A:
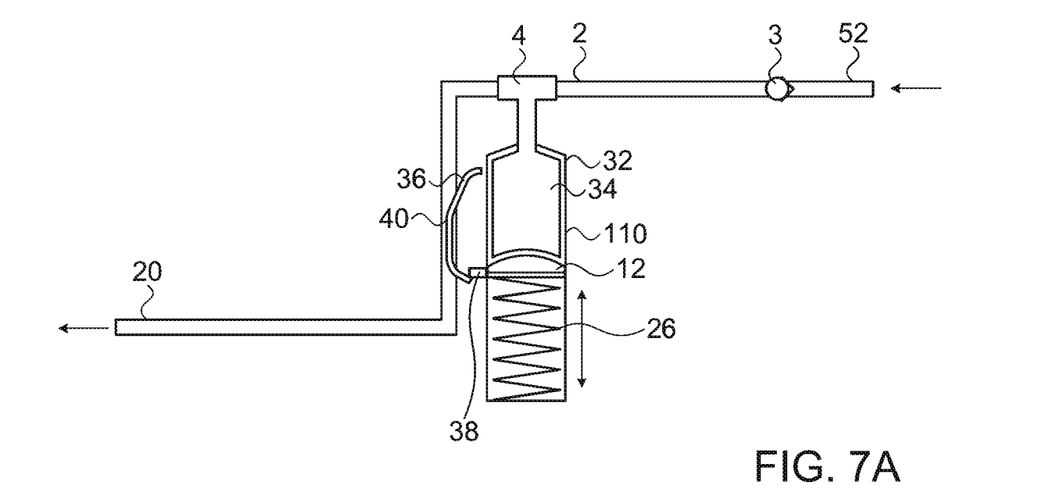
Figure 7B:
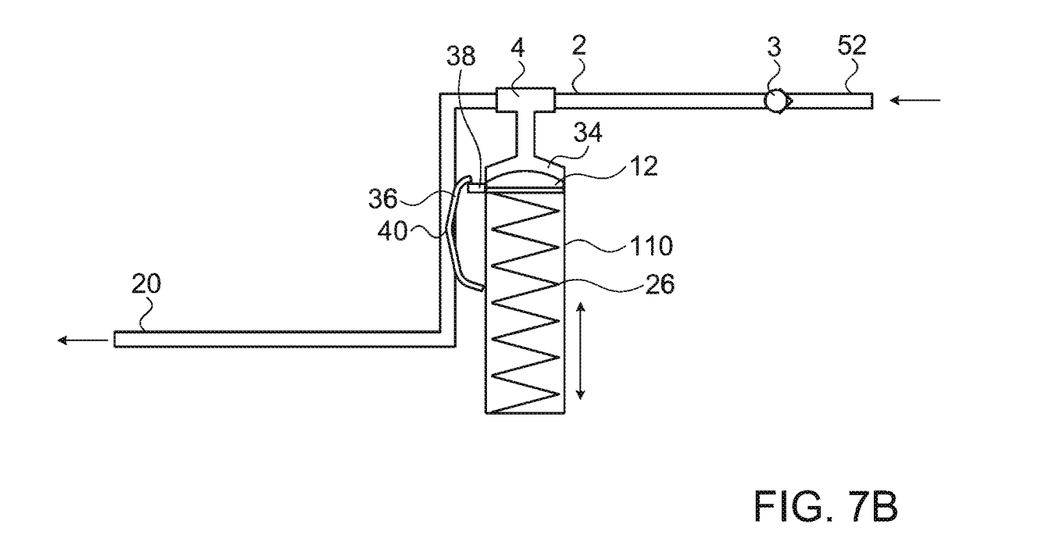

Turning now to FIGS. 7A and 7B that illustrate the almost identical embodiment shown in previous figures, FIGS. 6A and 6B, the only difference being that syringe 7 comprises an internal container made of an elastic material, for example of silicone rubber The advantages of this arrangement have been explained with reference to FIG. 4.

Figure 8:
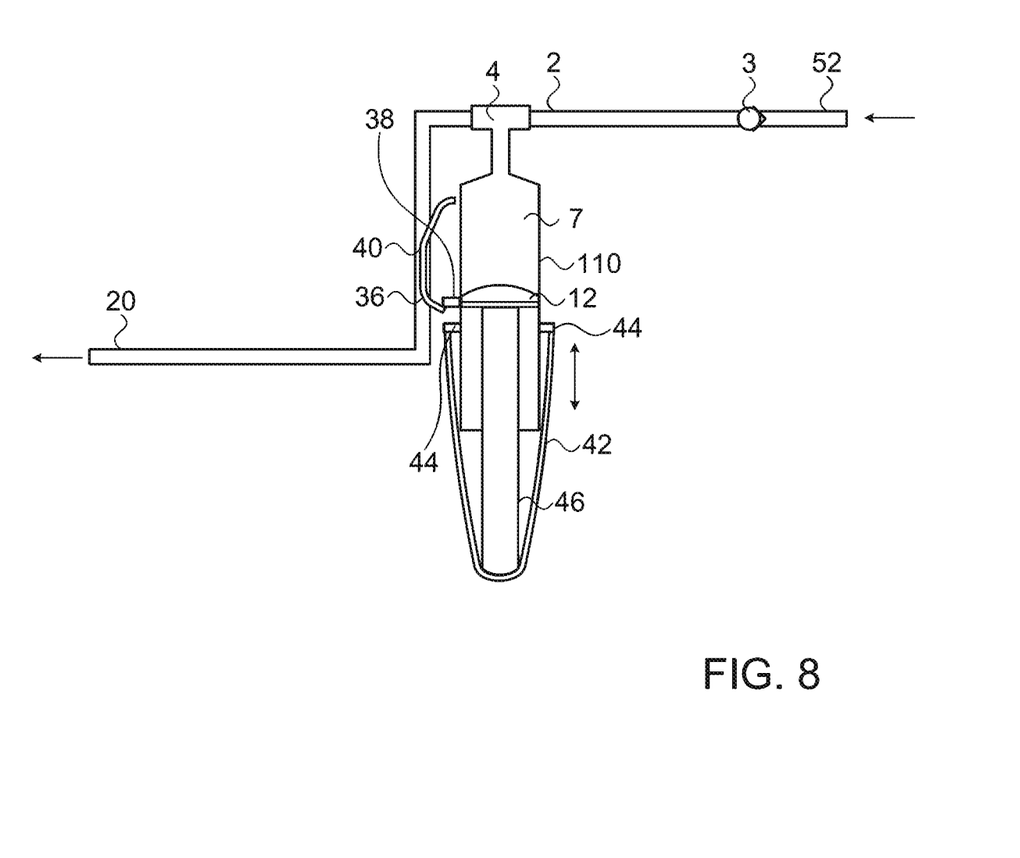
FIG. 8 is a schematic illustration of a mechanical pulse flow generation device according to some embodiments of the invention.

Referring now to FIG. 8, which is an illustration of an arrangement of a mechanical pulse device similar to the devices seen in FIGS. 6A and 6B. An elastic band 42 may be connected to projections 44 while being tensioned over a piston rod 46. The elastic band 42 thus replaces the compression spring 26 seen in previous embodiments, and being external can be easily replaced when necessary.

The pulsed flow generation device 110 can be an integral part of an infusion pump or may be connectable to any infusion pump known in the art.

Figure 9:
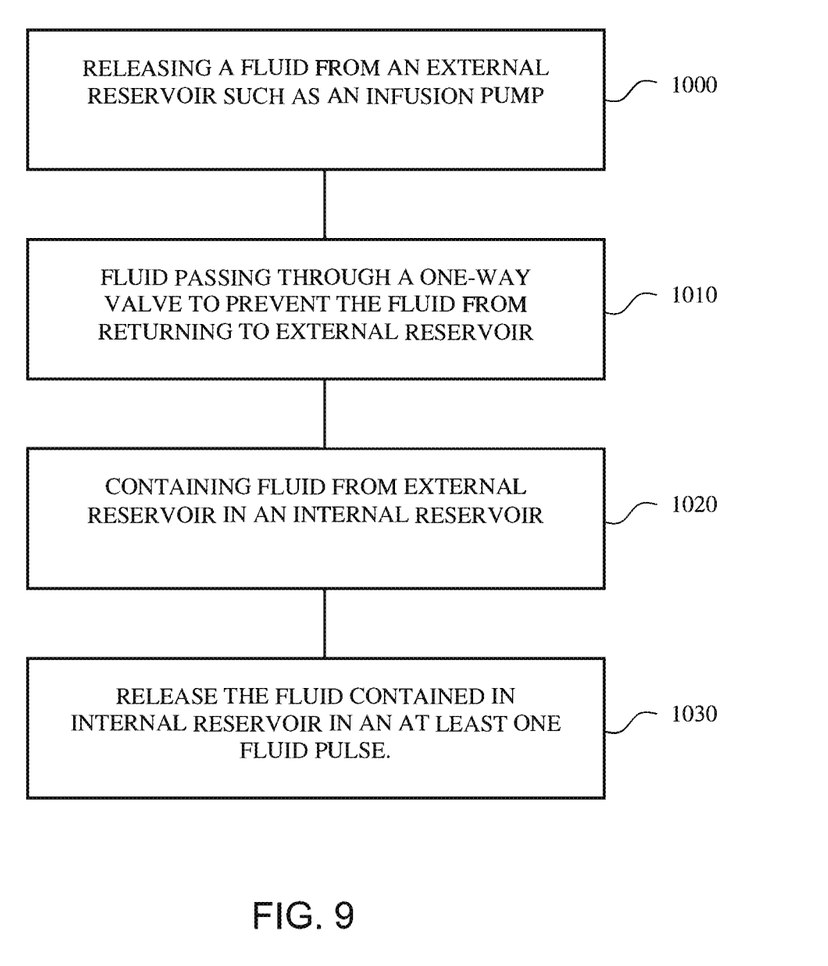
FIG. 9 is a flowchart of a method for converting a constant flow into a pulse flow according to some embodiments of the invention.

Reference is now made to FIG. 9 which is a flowchart of a method for converting a constant flow into a pulse flow according to an embodiment of the present invention. The method comprising the following steps:

Releasing a fluid, such as an infusion medicament, from an external reservoir such as an infusion pump [Block 1000]. The fluid may than pass through a one-way valve to prevent the fluid from returning to the external reservoir [Block 1010].

Since the fluid flowing form the external reservoir is prevented from returning to the reservoir by the one-way valve, and cannot pass another valve, such as an anti-siphon check valve, the fluid enters and contained in an internal reservoir, such as a syringe [Block 1020].

When the volume of fluid in the internal reservoir reaches a predefined value, for example, 30 ml, an actuation apparatus applies pressure on the fluid contained in the reservoir and thus releases the contained fluid in an at least one pulsed flow [Block 1030].

According to one embodiment of the present invention, the volume of fluid contained in the internal reservoir may be released in several consecutive pulses, each pulse having a volume which is relative to the number of pulses. For example, if the reservoir has been filled with 30 ml of fluid medication, it may be released in one pulse of 30 ml, or may be released in 3 consecutive pulses of 10 ml. each.

Figure 10A:
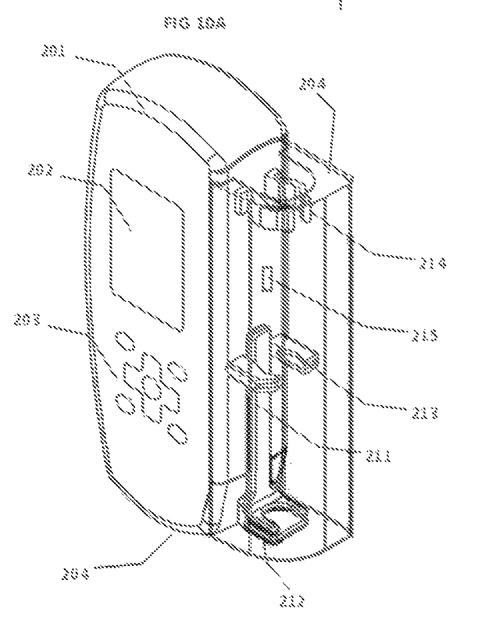
FIG. 10A is an illustration of an automatic pulse flow generation device according to some embodiments of the invention.

Reference is now made to FIG. 10A which is an illustration of an automatic pulse flow generation device according to some embodiments of the invention. Device 110 may include, a device body 201, made for example, from a rigid polymer, a screen 202, a keyboard 203 and a housing 204 for holding an internal reservoir and bidirectional pump, for example, in the form of syringe 250 illustrated in FIG. 11. Housing 204 may include holder 214 for holding the syringe. In some embodiments, holder 214 may include more than one component, for example, an internal reservoir holder 213 and a bidirectional pump holder 212. In the exemplary embodiment of FIG. 10, the internal reservoir holder 213 holds a syringe barrel and a bidirectional pump holder 212 holds a plunger of a piston. Housing 204 may further include a lever 211 to support the movement of the piston and a switch 215 for verifying that the internal reservoir was inserted into holder 214 and that a compatible internal reservoir is being used, for example in order to avoid administration errors such as overdosing or underdoing due to an insertion of a wrong internal reservoir.

Figure 10B:
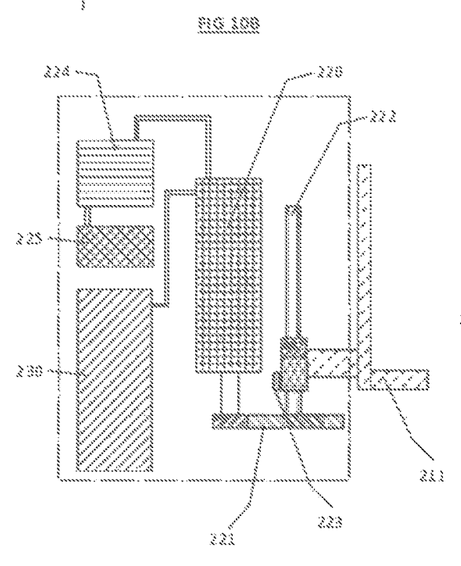
FIG. 10B is a high-level block diagram of the automatic pulse flow generation device of FIG. 10A according to some embodiments of the invention.

FIG. 10B is a high level block diagram that includes some of the components of device 110. Device 110 may further include a motor 220 (e.g., a servo motor) and a transmission 221 for transmitting a translational (or rotational) movement to lever 211 positioned over a shaft 222. Motor 220 may be powered by a battery 225 via a power supply unit 224. Device 110 may further include a controller 230.

Controller 230 may be configured to control at least some of the elements included in system 100 and device 110, for example, motor 220 and lever 211. Controller 230 may further be configured to control the bidirectional pump (e.g., pumps 12 and 251). Controller 230 may include any computation platform that may be configured to control system 100 according to code saved in a non-transitory memory associated with the controller, which when executed causes system 100 to perform methods of the invention. Additionally or alternatively controller 230 may executed instructions received from a user using a user interface associated with controller 230, for example, using keyboard 203 and/or screen 202. Screen 202 may be a touch screen or any other display known in the art. Controller 230 may include a processor (e.g., a CPU, microcontroller, programmable logic controller (PLC) and the like), a non-transitory memory for storing codes that when executed by the processor perform methods according to embodiments of the invention. Controller 230 may be associated with a user interface (e.g., a graphical user interface) that may include any devices that allow a user to communicate with the controller.

Controller 230 may control system 100 and device 110 to pump infusion fluid from the external reservoir to the internal reservoir and further pump an infusion fluid pulse from the internal reservoir to be injected by the catheter, the infusion liquid pulse may have a volume of at least 2 ml and a velocity of at least 5 ml/min.

Figure 11:
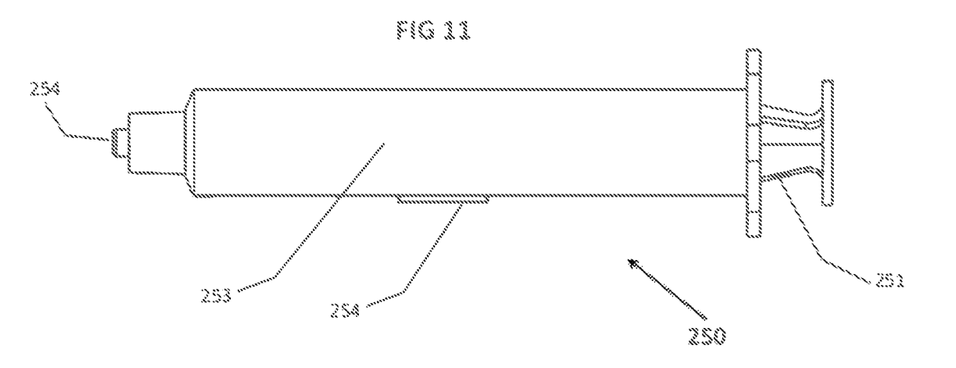
FIG. 11 is an illustration of a syringe according to some embodiments of the invention.

Reference is now made to FIG. 11 which illustrates an exemplary internal reservoir and bidirectional pump, to be attached to device 110 illustrated in FIG. 10 according to some embodiments of the invention. A syringe 250 may include an internal reservoir 253, for example, in the form of a barrel and a bidirectional pump 251, for example, in the form of a plunger pump and a piston located inside internal reservoir 253. Internal reservoir 253 may have a volume of 2-50 ml, for example, 15 ml. A Piston may be connected to a plunger pump (as illustrated) to form the bidirectional pump 251. Bidirectional pump 251 may be configured to pump infusion fluid from external reservoir, such as reservoir 1, to internal reservoir 253 and further pump an infusion fluid pulse from internal reservoir 253 to be injected by the catheter, the infusion liquid pulse may have a volume of at least 2 ml and a velocity of at least 5 ml/min Controller 230 may be configured to cause bidirectional pump 251 to pump infusion liquid to or from internal reservoir 253, for example, by controlling motor 220 to move lever 211 to push or pull the plunger of pump 251. Syringe 250 may further include an indicator 254 for identifying the syringe, for example, in order to verify that the syringe is in the correct volume or contains the correct substance.

In the embodiment of FIG. 11, the internal reservoir and the bidirectional pump are included in a single device, syringe 250. However, in other embodiments of the invention the internal reservoir and the bisectional pump may each be a standalone component connected together via tubing system. The bidirectional pump may be any pump configured to pump liquids to and from a reservoir. For example, the bidirectional pump may include: a plunger pump (as illustrated), a peristaltic pump, a roots-type pump or any other pump known in the art. The internal reservoir may include any container configured to hold infusion fluids. The internal reservoir may have a constant volume or a changeable volume that may vary with the amount of infusion fluid in the reservoir.

Figure 12:
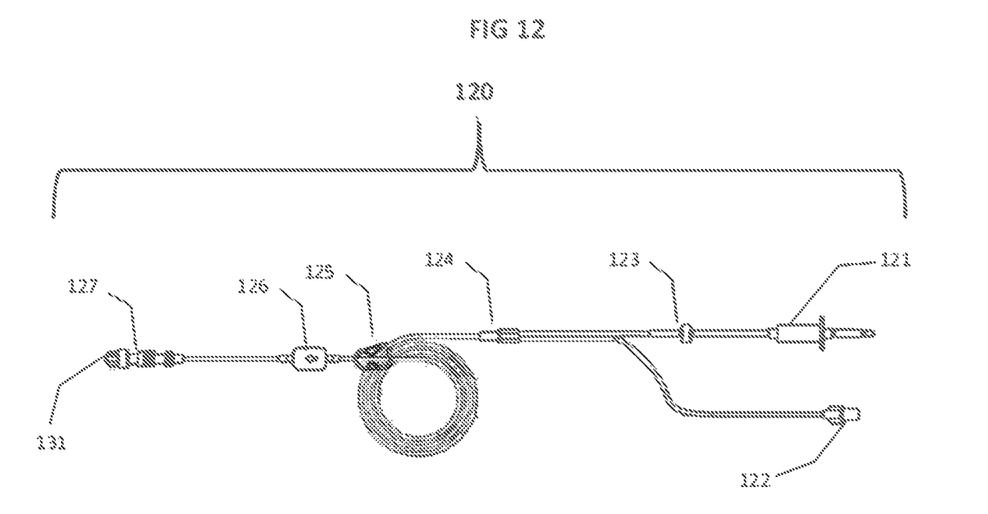
FIGS. 12 and 13 are illustrations of tubing systems according to some embodiments of the invention.
Figure 13:
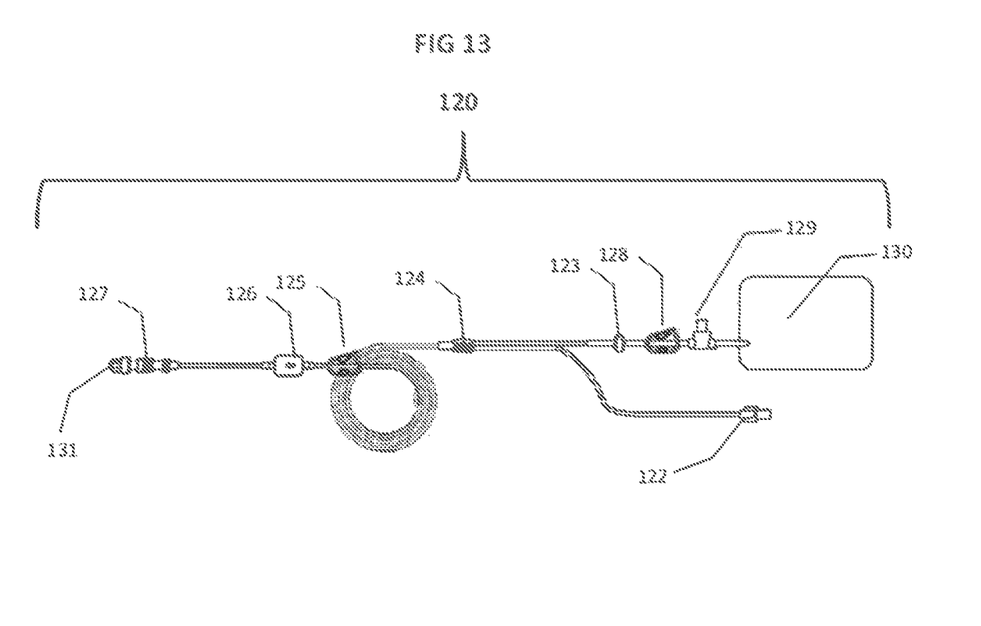

Reference is made to FIGS. 12 and 13 that are illustrations of tubing systems 120 according to some embodiments of the invention. Both systems 120 of FIGS. 12 and 13 may include one-way check valve 123, Y connector 124, syringe connector 122, patient clamp 125, filer 126, anti-siphon one way check valve 127 and outlet port 131. The tubing system of FIG. 12 further includes piercing device 121 at the inlet port proximate to valve 123. The tubing system of FIG. 13 may further include an external reservoir 130, a medical team clamp 128 and a filling port 129.

Figure 14:
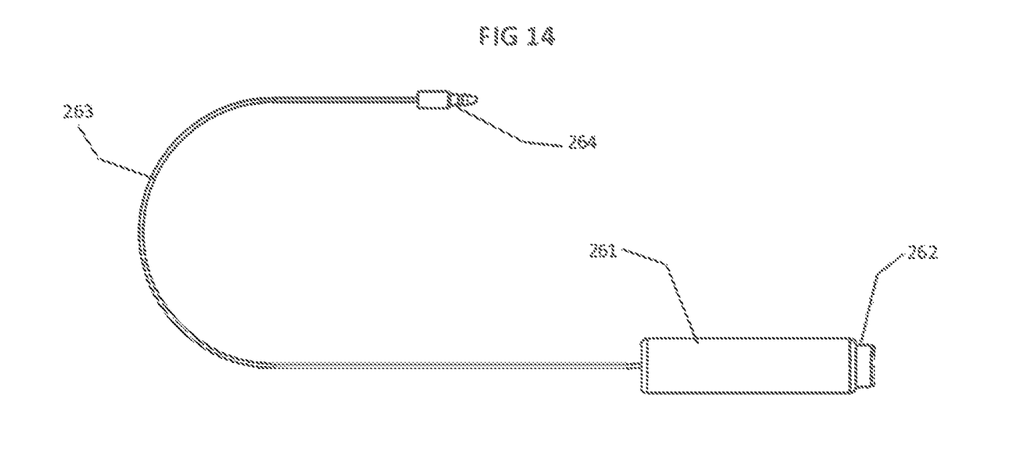
FIG. 14 is an illustration of a manual controller for controlling an automatic pulse flow generation device according to some embodiments of the invention.

Reference is made to FIG. 14 that is an illustration of a manual controller (e.g., controller 260) for controlling device 110 to apply a Patient Control Analgesia (PCA) and/or a Clinician Bolus by operating system 100 to inject infusion liquid pulse, for example, upon a request from the patient or a decision made by a medical professional. The injected infusion liquid pulse may have a volume of at least 2 ml and a velocity of at least 5 ml/min. The manual controller may include a housing 261, a push button 262 to be pushed by the patient, a wire 263 and a plug 264. The manual controller may be configured to cause an application of a predetermined amount of medication at a predetermined velocity, for example, 3 ml at 5 ml/min when the patient/clinician pushes button 262, regardless of the frequency of infusion liquid pulse programed in automatic device 110. The manual controller may be operated in addition to the automatic administration programed in automatic device 110 or separately when no administration is programed in automatic device 110. It should be appreciated by those skilled in the art that in order to avoid overdosing, a lock time period during which additional pulses cannot be initiated by the patient may be set. It should be further appreciated that the predetermined amount of medication released by the patient and/or clinician may be reduced from the total volume of liquid in the internal reservoir and thus from the total volume of medication given to the patient in a given time interval.

Figure 15:
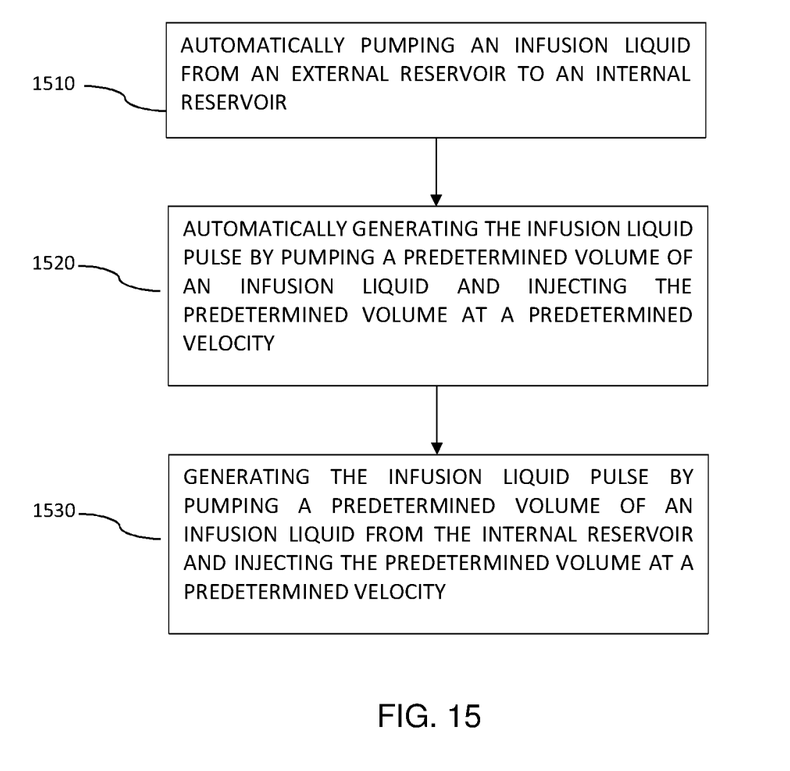
FIG. 15 is a flowchart of a method of administrating an infusion liquid pulse according to some embodiments of the invention.

Reference is made to FIG. 15 which is a flowchart of a method of administrating an infusion liquid pulse according to some embodiments of the invention. The method of FIG. 15 may be performed by pulse infusion system 100, disclosed above. In box 1510 the method may include automatically pumping an infusion liquid from an external reservoir (e.g., reservoir 1) to an internal reservoir (e.g., internal reservoirs 7 or 253) included in a pulse infusion system, the external reservoir may be adapted to contain infusion fluids. System 100 may automatically pump the infusion liquid from the external reservoir every predetermined amount of time, for example, at least once in every 90 minutes, or every shorter periods of time. The infusion liquid may be pump using bidirectional pump.

In box 1520, the method may include automatically generating the infusion liquid pulse by pumping a predetermined volume of an infusion liquid from the internal reservoir and injecting the predetermined volume at a predetermined velocity, the predetermined volume may be at least 2 ml and the predetermined velocity may be at least 5 ml/min. The infusion liquid pulse may be generated using the bidirectional pump. The infusion liquid pulse may be injected to a patient via a catheter. In some embodiments, the predetermined volume may be between 2 ml to 15 ml. In some embodiments, the predetermined velocity may be between 5 ml/min to 30 ml/min. In some embodiments, the pressure of the infusion liquid pulse inside the internal reservoir may be any predetermined pressure to enable injecting the predetermined volume at a predetermined velocity, for example in the range of 2-4 bars.

In box 1530, the method may include manually generating the infusion liquid pulse by pumping a predetermined volume of an infusion liquid from the internal reservoir and injecting the predetermined volume at a predetermined velocity, the predetermined volume may be at least 2 ml and the predetermined velocity may be at least 5 ml/min. The infusion liquid pulse may be generated by controlling a manual controller (e.g., by pushing button 262) to operate the bidirectional pump. The infusion liquid pulse may be injected to a patient via a catheter. In some embodiments, the predetermined volume may be between 2 ml to 15 ml. In some embodiments, the predetermined velocity may be between 5 ml/min to 30 ml/min. In some embodiments, the pressure of the infusion liquid pulse inside the internal reservoir may be any predetermined pressure to enable injecting the predetermined volume at a the predetermined velocity, for example, in the range of 2-4 bars.

In some embodiments, the method may include repeating the automatic generation of the infusion liquid pulse every predetermined duration of time, for example, at least once in every 90 minutes. In some embodiments, the method may include repeating the automatically pumping the infusion liquid from the external reservoir and automatic generation of the infusion liquid pulse every the same predetermined amount of time.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of administrating an infusion liquid pulse, comprising:
    automatically pumping, by a bidirectional pump, an infusion liquid from an external reservoir to an internal reservoir included in a pulse infusion system, wherein the external reservoir is adapted to contain infusion fluids;
    automatically generating the infusion liquid pulse by pumping, by the bidirectional pump from the internal reservoir a predetermined volume of an infusion liquid and injecting the predetermined volume by a catheter at a predetermined velocity, wherein the predetermined volume is at least 2 milliliter (ml) and the predetermined velocity is at least 5 milliliter/minute (ml/min); and
    controlling the bidirectional pump by a controller.

2. The method of claim 1, further comprising repeating the automatic generation of the infusion liquid pulse every first predetermined duration of time.

3. The method of claim 2, further comprising repeating the automatic pumping of the infusion liquid every second predetermined duration of time.

4. The method of claim 3, wherein the first predetermined duration of time is equal to the second predetermined duration of time.

5. The method of claim 2, wherein the first predetermined duration of time is at least once in every 90 minutes.

6. The method of claim 1, wherein the predetermined volume is between 2 ml and 15 ml.

7. The method of claim 1, wherein the predetermined velocity is between 5 ml/min to 30 ml/min.

8. The method of claim 1, further comprising:
    manually operating a manual controller, by a patient, to cause an additional injection of an infusion liquid pulse having a volume of at least 2 ml and a velocity of at least 5 ml/min.

9. The method of claim 1, further comprising receiving from a user values of the volume and the velocity.

10. The method of claim 1, further comprising controlling a frequency at which the pulses are injected.

11. The method of claim 10, wherein the pulses are injected at a frequency between once in every 90 minutes and once in every 10 minutes.

* * * * *